(12) United States Patent
Jun et al.

(10) Patent No.: US 10,993,993 B2
(45) Date of Patent: *May 4, 2021

(54) PHARMACEUTICAL COMPOSITION FOR TREATING MUSCLE ATROPHY OR SARCOPENIA INCLUDING GLUCAGON-LIKE PEPTIDE (GLP-1) OR GLP-1 RECEPTOR AGONIST

(71) Applicant: IMMUNOFORGE CO., LTD., Gyeonggi-do (KR)

(72) Inventors: Hee Sook Jun, Incheon (KR); Eun Young Park, Incheon (KR); Yeon Hee Hong, Sejong (KR)

(73) Assignee: IMMUNOFORGE CO., LTD., Gyeonggi-do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/160,371

(22) Filed: Oct. 15, 2018

(65) Prior Publication Data

US 2019/0046614 A1 Feb. 14, 2019

Related U.S. Application Data

(63) Continuation-in-part of application No. 15/577,299, filed as application No. PCT/KR2016/005615 on May 27, 2016, now Pat. No. 10,751,392.

(30) Foreign Application Priority Data

May 28, 2015 (KR) .......................... 10-2015-0074985

(51) Int. Cl.
- *A61K 38/26* (2006.01)
- *C07K 14/605* (2006.01)
- *A61P 21/00* (2006.01)

(52) U.S. Cl.
CPC .............. *A61K 38/26* (2013.01); *A61P 21/00* (2018.01); *C07K 14/605* (2013.01); *C07K 2319/30* (2013.01)

(58) Field of Classification Search
CPC ..................................................... A61K 38/26
See application file for complete search history.

(56) References Cited

U.S. PATENT DOCUMENTS

| | | | |
|---|---|---|---|
| 8,853,154 B2 * | 10/2014 | Cload | A61K 47/60 514/4.8 |
| 9,012,606 B2 * | 4/2015 | Chung | C07K 14/8125 530/350 |
| 2009/0232807 A1 * | 9/2009 | Glaesner | C07K 14/605 424/134.1 |
| 2012/0282255 A1 * | 11/2012 | Plucinski | A61K 38/26 424/134.1 |

FOREIGN PATENT DOCUMENTS

| | | |
|---|---|---|
| JP | 2013-507341 A | 3/2013 |
| JP | 5695097 B2 | 7/2013 |
| KR | 10-0837363 B1 | 6/2008 |
| KR | 10-1439783 B1 | 9/2014 |
| WO | WO 2006/081997 | 8/2006 |
| WO | WO 2007/088123 | 8/2007 |
| WO | WO 2014/096148 A1 | 6/2014 |

OTHER PUBLICATIONS

Ikejima et al., Diabetes, 67 (supplement 1), 2018.*
Chuan-An Shen et al: "Effects of glucagon-like peptide 1 on glycemia control and its metabolic consequence after severe thermal injurystudies in an animal model", Surgery, Mosby, Inc, US, vol. 149, No. 5, Nov. 24, 2010 (Nov. 24, 2010), pp. 635-644, XP028193515.
Elahi D, et al., GLP-1(32-36)amide, a novel pentapeptide cleavage product of GLP-1, modulates whole body glucose metabolism in dogs, Peptides, Jun. 14, 2014, vol. 59, p. 20-24.
Fanzani A, et al., Molecular and cellular mechanisms of skeletal muscle atrophy: an update, Journal of Cachexia, Sarcopenia and Muscle, Jun. 7, 2012, vol. 3, No. 3, p. 163-179.
Hisashi Kuwata, Hiroshi Seino, DPP-4 inhibitor, hepatobiliary pancreas, Nov. 2012, vol. 65, No. 5, p. 809-816.
Junichiro Miyagawa, Mitsuyoshi Namba, DPP-4 inhibitor (incretin enhancer), Japanese clinical, 2012, 70, extra No. 3 (latest clinical diabetes studies (upper), p. 682-688.
Knippenberg S, et al., Intracerebroventricular injection of encapsulated human mesenchymal cells producing glucagon-like peptide 1 prolongs s urvival in a mouse model of ALS, PLoS ONE, Jun. 20, 2012, vol. 7 , No. 6, e36857, doi: 10.1371/journal.pone.0036857.
Li Y, et al., Exendin-4 ameliorates motor neuron degeneration in cellular and animal models of amyotrophic lateral sclerosis, PLoS ONE, Feb. 23, 2012, vol. 7, No. 2, e32008, doi: 10.1371/journal.pone.0032008.
Sun H, et al., Therapeutic potential of N-acetyl-glucagon-like peptide-1 in primary motor neuron cultures derived from non-transgenic and SOD 1-G93A ALS mice, Cellular and Molecular Neurobiology, 2013, vol. 33 , No. 3, p. 347-357.
Office Action issued in Japanese Patent Application No. 2018-514760, dated Oct. 9, 2018.

(Continued)

*Primary Examiner* — Gyan Chandra

(74) *Attorney, Agent, or Firm* — Knobbe Martens Olson & Bear LLP

(57) ABSTRACT

A pharmaceutical composition for preventing or treating muscle atrophy or sarcopenia including glucagon-like peptide-1 (GLP-1), a GLP-1 fragment, a GLP-1 secretion enhancer, a GLP-1 degradation inhibitor, a GLP-1 receptor (GLP-1R) agonist, or exendin-4, and a method of treating muscle atrophy or sarcopenia by using the pharmaceutical composition. When the pharmaceutical composition is administered to a subject having sarcopenia or muscle atrophy, reduced body weight, skeletal muscle mass, and grip strength, which are caused by sarcopenia or muscle atrophy, and expression levels of genes involved in muscle production may be restored to normal states. The composition may be widely applied to the development of effective therapeutic agents for sarcopenia or muscle atrophy.

6 Claims, 12 Drawing Sheets

Specification includes a Sequence Listing.

(56) References Cited

OTHER PUBLICATIONS

Supplemental Search Report issued in European Patent Application No. 1680033.6, dated Nov. 30, 2018.
Amato et al. 2014. Exogenous glucagon-like peptide 1 reduces contractions in human colon circular muscle, *Journal of Endocrinology*, 221(1):29-37.
Cetrone et al. 2014. Effects of the antidiabetic drugs on the age-related atrophy and sarcopenia associated with Diabetes Type II. *Current Diabetes Review*, 10(4):231-237.
International Search Report dated Aug. 8, 2016 in International Application No. PCT/KR2016/005615 filed May 27, 2016, 8 pages.
Written Opinion dated Aug. 8, 2016 in International Application No. PCT/KR2016/005615 filed May 27, 2016, 6 pages.
Ito Washin et al., Classification and kinds of side effects that can be predicted from pharmacological features, Pharmacy, vol. 6 3, No. 2, pp. 273 to 277 (2012).
Office Action in Japanese Patent Application No. 2018-514760 dated Mar. 3, 2020.
Office Action in Japanese Patent Application No. 2018-514760, dated Oct. 6, 2020.
Imahori et al., Biochemical Dictionary, Tokyo Kagaku Dojin Co., Ltd., vol. 3(5), p. 109, Jul. 1, 2002.

\* cited by examiner

[FIG. 1]
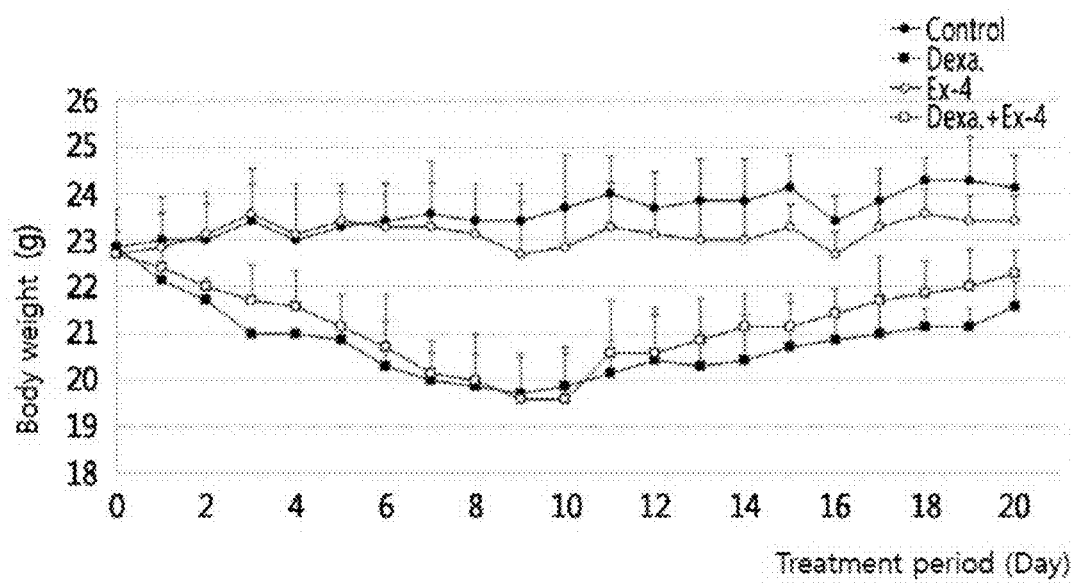

[FIG. 2]
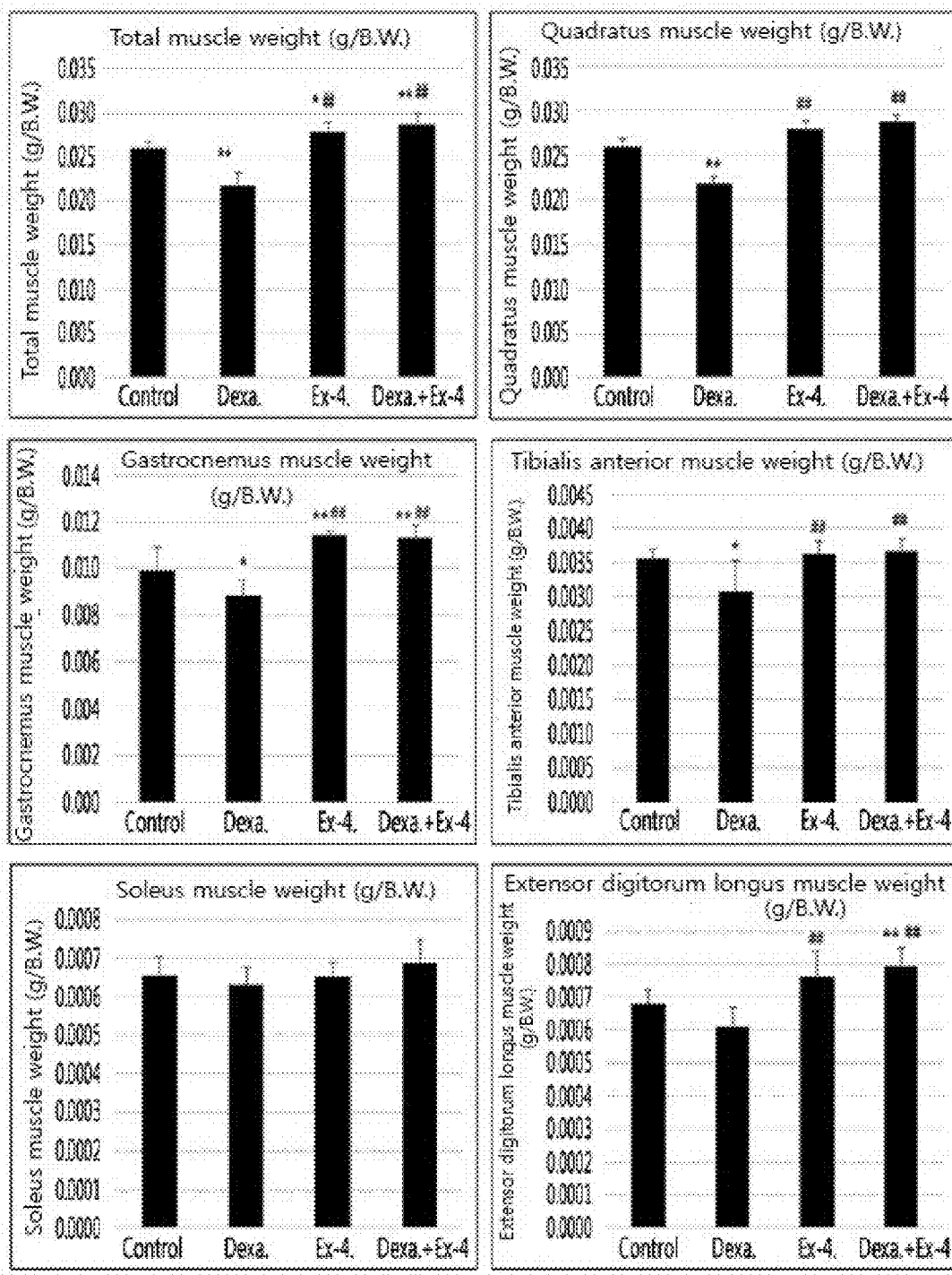

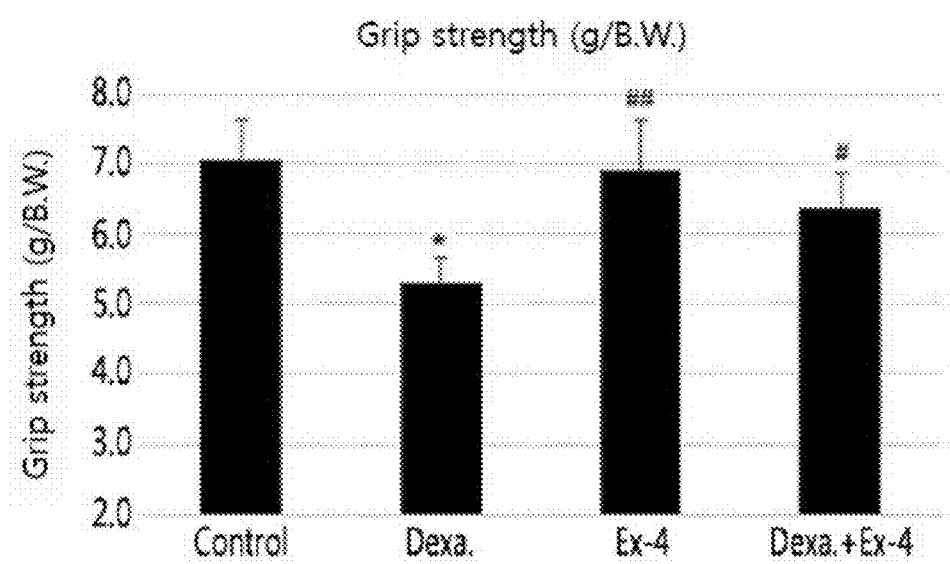
[FIG. 3]

[FIG. 4]
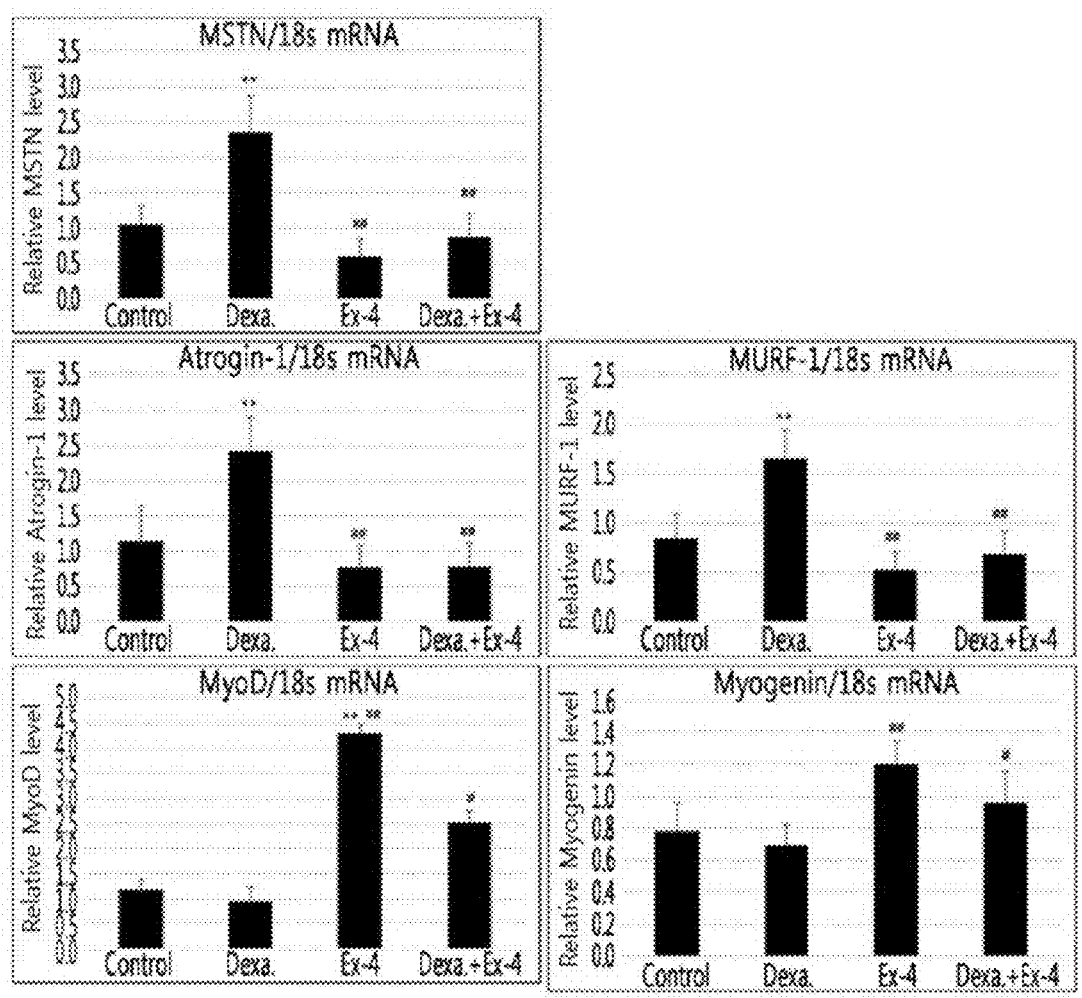

[FIG. 5]
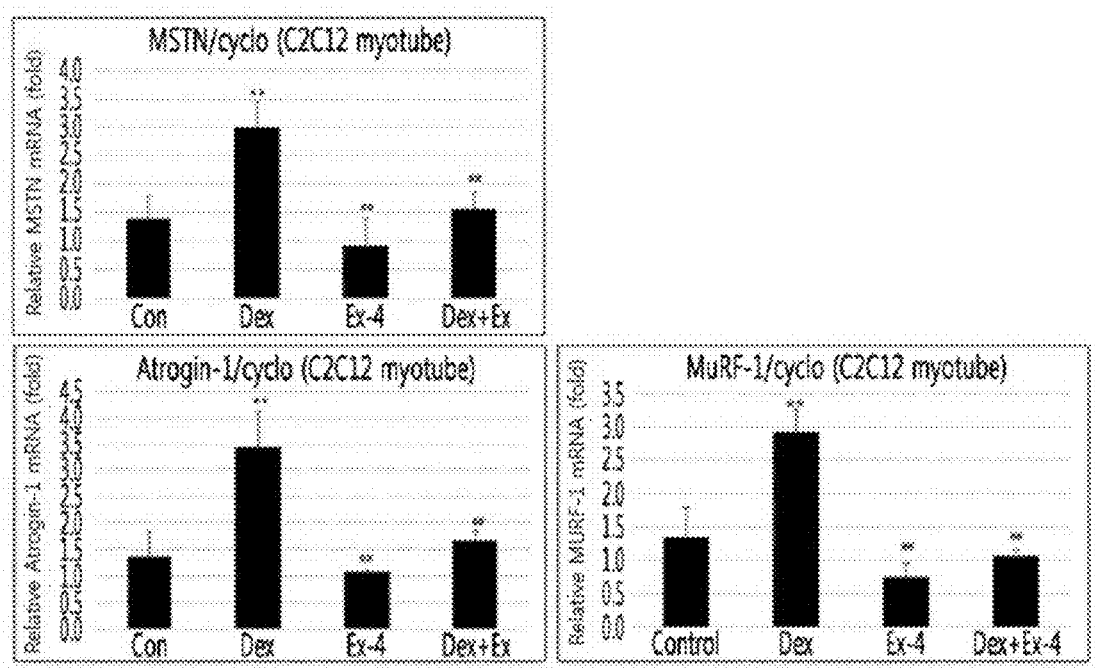

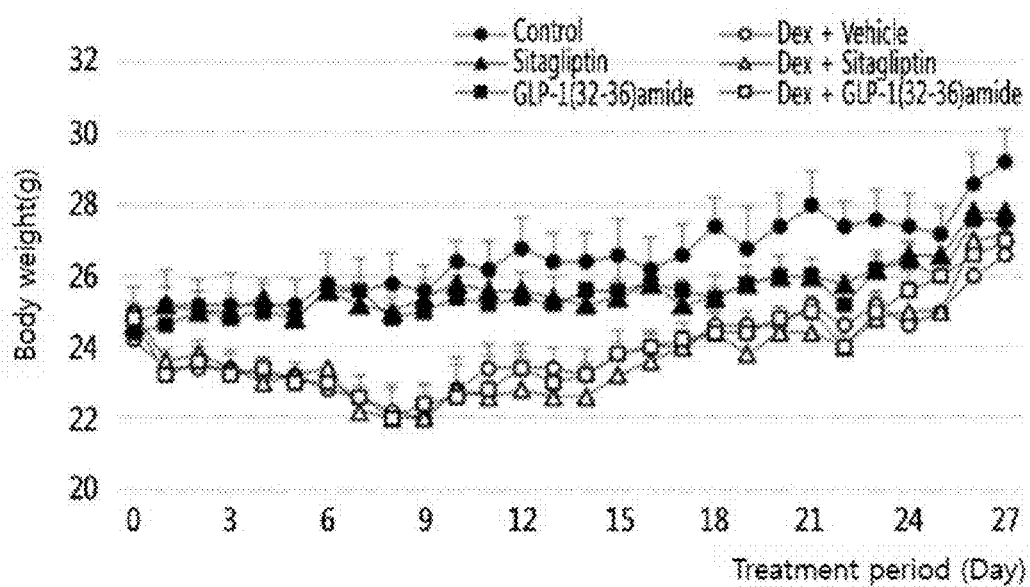
[FIG. 6]

[FIG. 7]
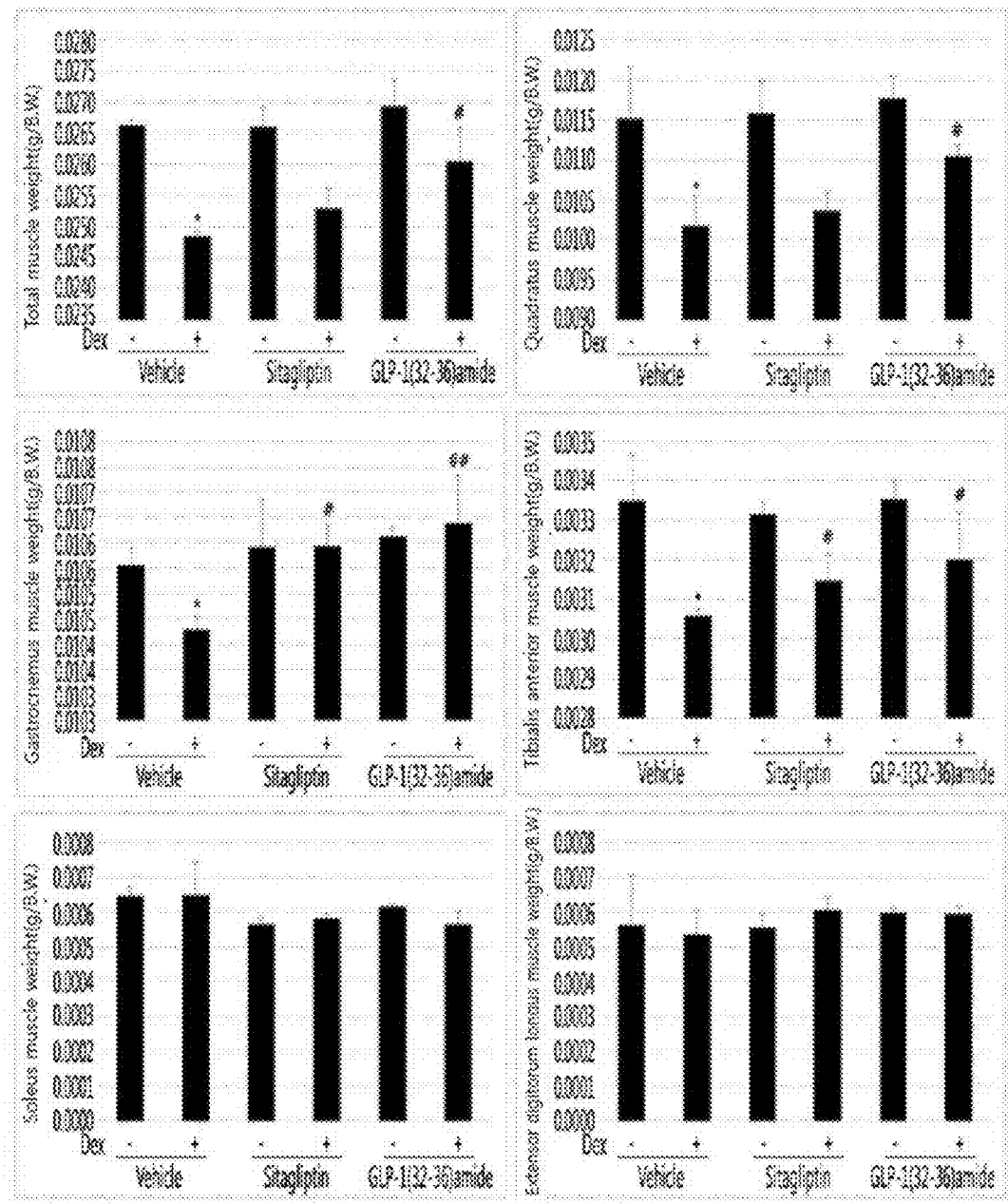

[FIG. 8]
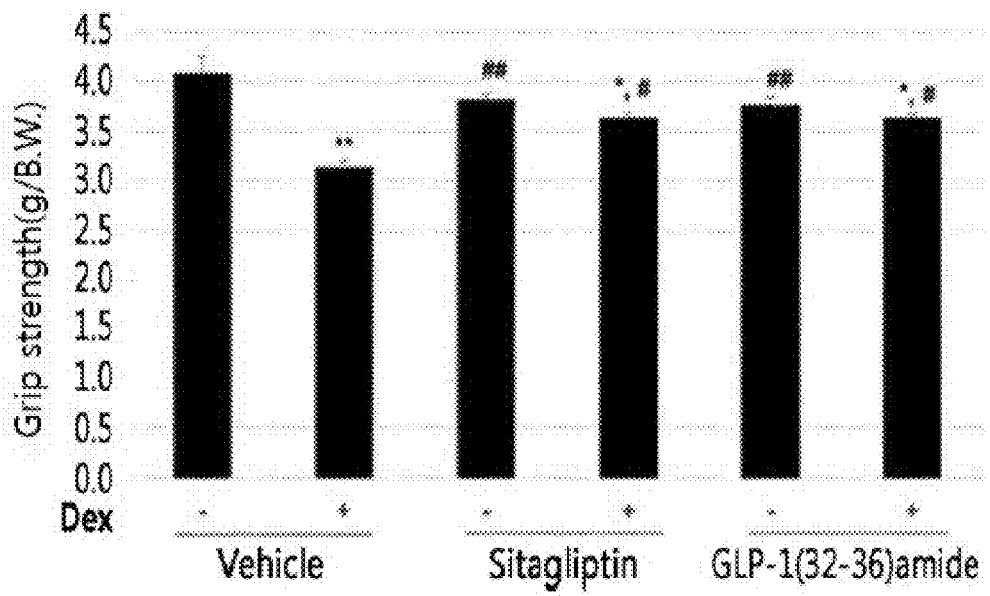
[FIG. 9]
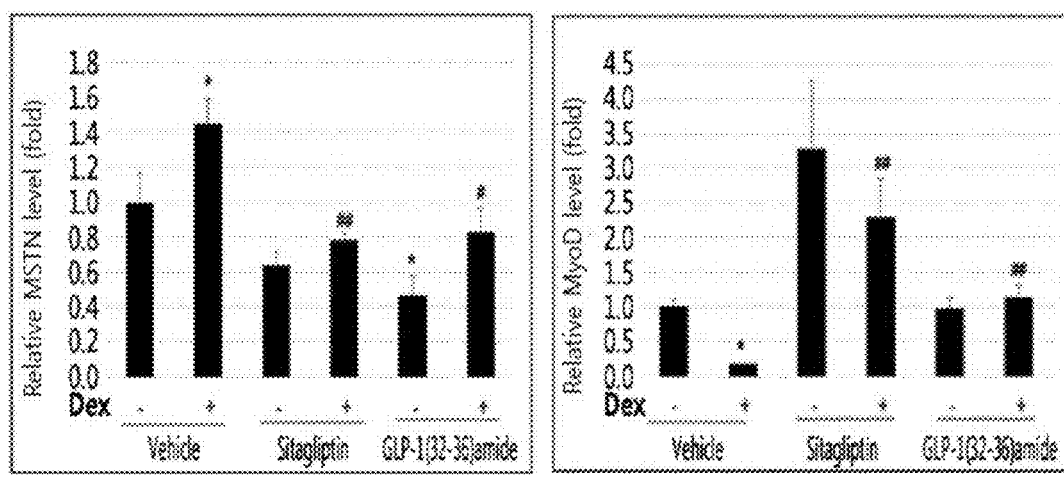

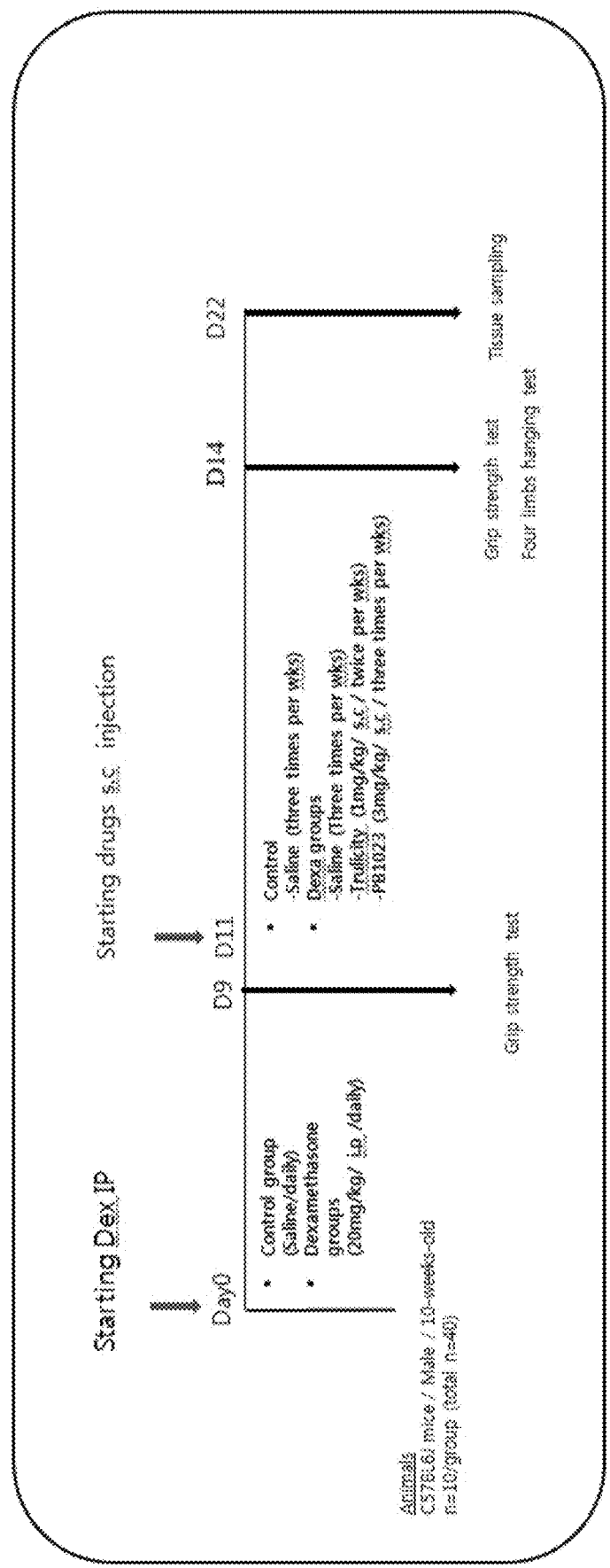
[FIG. 10]

[FIG. 11]
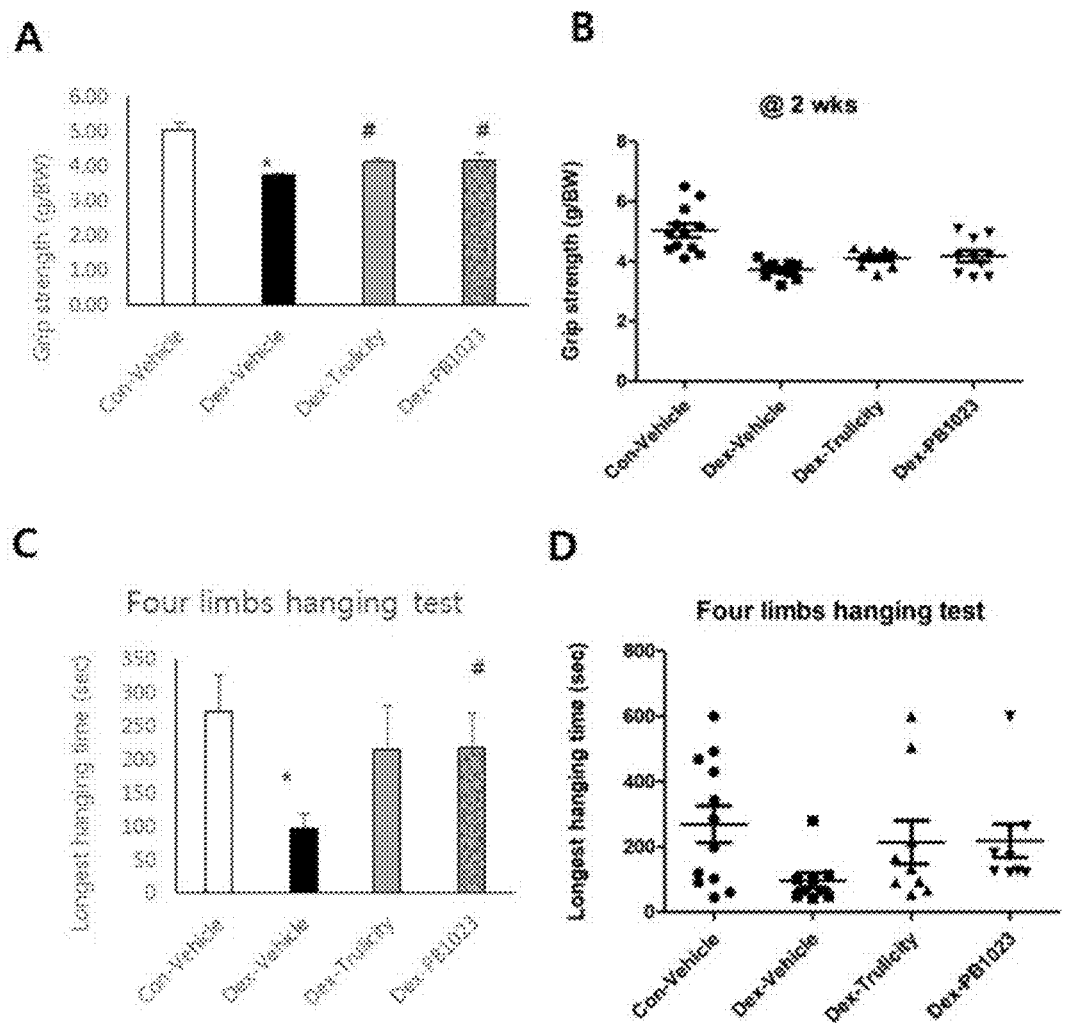

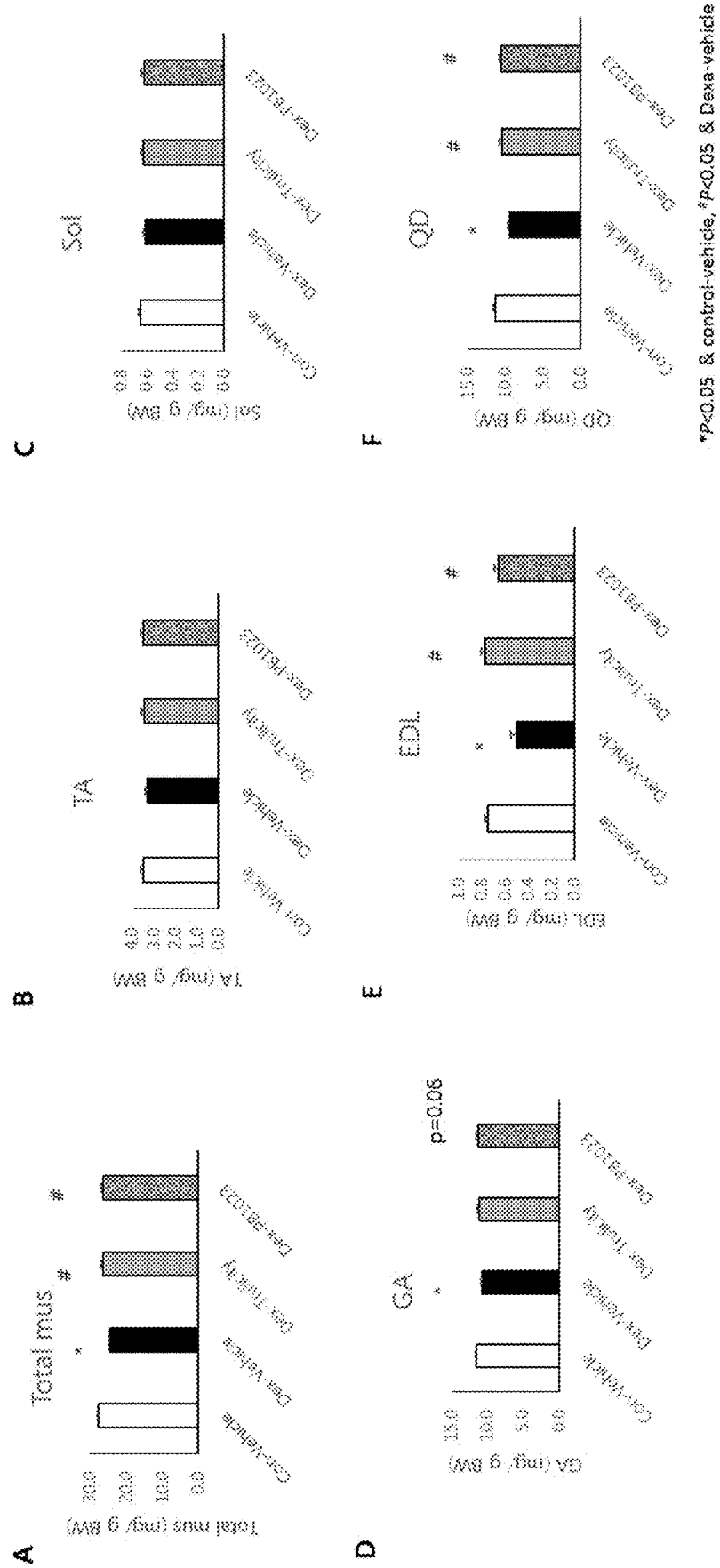
[FIG. 12]

FIG. 13

SEQUENCE LISTING

```
<160> NUMBER OF SEQ ID NOS: 5

<210> SEQ ID NO 1
<211> LENGTH: 39
<212> TYPE: PRT
<213> ORGANISM: Artificial Sequence
<220> FEATURE:
<223> OTHER INFORMATION: recombinant Exendin-4

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 2
<211> LENGTH: 5
<212> TYPE: PRT
<213> ORGANISM: Artificial Sequence
<220> FEATURE:
<223> OTHER INFORMATION: GLP-1(32-36)amide

<400> SEQUENCE: 2

Leu Val Lys Gly Arg
1               5

<210> SEQ ID NO 3
<211> LENGTH: 37
<212> TYPE: PRT
<213> ORGANISM: Homo sapiens

<400> SEQUENCE: 3

His Asp Glu Phe Glu Arg His Ala Glu Gly Thr Phe Thr Ser Asp Val
1               5                   10                  15

Ser Ser Tyr Leu Glu Gly Gln Ala Ala Lys Glu Phe Ile Ala Trp Leu
            20                  25                  30

Val Lys Gly Arg Gly
        35
```

```
<210> SEQ ID NO 4
<211> LENGTH: 30
<212> TYPE: PRT
<213> ORGANISM: Homo sapiens

<400> SEQUENCE: 4

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 5
<211> LENGTH: 275
<212> TYPE: PRT
<213> ORGANISM: Artificial Sequence
<220> FEATURE:
<223> OTHER INFORMATION: dulaglutide

<400> SEQUENCE: 5

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Ser Gly Gly Gly Ser Gly Gly Gly Ser Ala Glu
        35                  40                  45

Ser Lys Tyr Gly Pro Pro Cys Pro Pro Cys Pro Ala Pro Glu Ala Ala
    50                  55                  60

Gly Gly Pro Ser Val Phe Leu Phe Pro Pro Lys Pro Lys Asp Thr Leu
65                  70                  75                  80

Met Ile Ser Arg Thr Pro Glu Val Thr Cys Val Val Val Asp Val Ser
                85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
        115                 120                 125

Tyr Arg Val Val Ser Val Leu Thr Val Leu His Gln Asp Trp Leu Asn
130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
        195                 200                 205

Glu Trp Glu Ser Asn Gly Gln Pro Glu Asn Asn Tyr Lys Thr Thr Pro
210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
            260                 265                 270

Ser Leu Gly
        275
```

PHARMACEUTICAL COMPOSITION FOR TREATING MUSCLE ATROPHY OR SARCOPENIA INCLUDING GLUCAGON-LIKE PEPTIDE (GLP-1) OR GLP-1 RECEPTOR AGONIST

RELATED APPLICATIONS

This application is a continuation-in-part of U.S. patent application Ser. No. 15/577,299, filed Nov. 27, 2017, which is the U.S. National Phase entry under 35 U.S.C. 371 of PCT/KR2016/005615, filed May 27, 2016, which claims priority to Korean Patent Application No. 10-2015-0074985, filed May 28, 2015, the entire content of which is incorporated herein by reference.

SEQUENCE LISTING

The present application is being filed along with a Sequence Listing in electronic format. The Sequence Listing is provided as a file entitled SequenceListing.TXT, created Oct. 15, 2018, which is 4 kb in size. The information is the electronic format of the Sequence Listing is incorporated herein by reference in its entirety.

TECHNICAL FIELD

The present invention relates to a pharmaceutical composition for treating muscle atrophy or sarcopenia including a glucagon-like peptide-1 (GLP-1) or a GLP-1 receptor agonist, and more particularly, to a pharmaceutical composition for preventing or treating muscle atrophy or sarcopenia including a glucagon-like peptide-1 (GLP-1), a GLP-1 fragment, a GLP-1 secretion enhancer, a GLP-1 degradation inhibitor, a GLP-1 receptor (GLP-1R) agonist, or exendin-4, and a method of treating muscle atrophy or sarcopenia by using the pharmaceutical composition.

BACKGROUND ART

Sarcopenia caused by degeneration of spinal nerve, motor nerve, or skeletal muscle fiber is a representative intractable disease of which the etiology has not yet been clarified. According to studies conducted thus far, it is known that contraction of skeletal muscles does not occur due to degeneration of motor nerves inducing contraction of skeletal muscles, normal contraction of skeletal muscles does not occur due to reduced expression (sarcopenia) or modification of proteins involved in muscle contraction in the skeletal muscles, and motor nerves or skeletal muscles are modified to fibrous tissues in the long term. As such, since the underlying cause of sarcopenia has not been identified, and methods capable of preventing or restoring degeneration of motor nerves or skeletal muscles have not been developed, studies are presently underway in order to develop a method of slowing the progression of sarcopenia.

As a method of slowing the progression of sarcopenia, a method of inhibiting muscle atrophy caused by degenerative or progressive modification of myocytes, which is a kind of sarcopenia, is mainly used. For example, WO 2007/088123 discloses a therapeutic agent for muscle atrophy including a nitrooxy derivative as an active ingredient, and WO 2006/081997 discloses a therapeutic agent for muscle atrophy including atraric acid or a derivative thereof as an active ingredient. However, since these therapeutic agents including the compounds as the active ingredients act on smooth muscles or cardiac muscles which are not associated with muscle atrophy, as well as on skeletal muscles in which muscle atrophy occurs, a variety of major or minor side effects may be caused, and therefore, the therapeutic agents do not have practical application.

Although hormone agents have side effects, their side effects are remarkably reduced as compared with chemical agents, and the hormone agents have bio-friendly properties. Therefore, development of hormone-like agents is being accelerated.

Meanwhile, muscle atrophy is a disease in which muscles of the legs and arms are atrophied, and represented by amyotrophic lateral sclerosis and spinal progressive muscular atrophy, which are known as diseases caused by progressive modification of motor nerve fibers and cells in the spinal cord.

Specifically, spinal muscular atrophy is known as a genetic disorder and neuromuscular disease caused by modification of motor neurons in the spinal cord. Further, amyotrophic lateral sclerosis is characterized by intractable, irreversible neurodegenerative changes due to the death of upper motor neurons and lower motor neurons in the cerebrum and spinal cord, and its main cause is known to be lack of nerve growth factor and neuritis.

SUMMARY OF THE INVENTION

The present inventors have made intensive efforts to develop an agent capable of effectively treating muscle atrophy or sarcopenia or effectively slowing progression thereof, and as a result, they found that a glucagon-like peptide-1 (GLP-1) or a GLP-1 receptor agonist may alleviate symptoms of sarcopenia, thereby completing the present invention.

An object of the present invention is to provide a pharmaceutical composition for preventing or treating muscle atrophy or sarcopenia.

Another object of the present invention is to provide a method of treating muscle atrophy or sarcopenia by using the pharmaceutical composition.

Advantageous Effects

When a pharmaceutical composition for preventing or treating muscle atrophy or sarcopenia provided in the present invention is administered to a subject having sarcopenia or muscle atrophy, reduced body weight, skeletal muscle mass, and grip strength, which are caused by sarcopenia or muscle atrophy, and expression levels of genes involved in muscle production may be restored to normal states, and therefore, the composition may be widely applied to the development of effective therapeutic agents for sarcopenia or muscle atrophy.

BRIEF DESCRIPTION OF THE DRAWINGS

FIG. 1 is a graph showing changes in the body weights which were measured in control mice, comparative mice, muscle atrophy-induced mice, and muscle atrophy-treated mice while they were raised for 20 days;

FIG. 2 is a graph showing results of comparing weights of respective skeletal muscles which were obtained from control mice, comparative mice, muscle atrophy-induced mice, and muscle atrophy-treated mice;

FIG. 3 is a graph showing results of comparing grip strengths which were measured in control mice, comparative mice, muscle atrophy-induced mice, and muscle atrophy-treated mice;

FIG. 4 is a graph showing results of comparing expression levels of muscle protein-destroying genes (myostatin, atrogin-1, and MuRF1) and muscle protein-producing genes (MyoD and myogenin) in control mice, comparative mice, muscle atrophy-induced mice, and muscle atrophy-treated mice;

FIG. 5 is a graph showing results of comparing expression levels of muscle atrophy-related genes (myostatin, atrogin-1, and MuRF1) in control myocytes, muscle atrophy symptom-induced myocytes, comparative myocytes, and muscle atrophy symptom-treated myocytes;

FIG. 6 is a graph showing changes in body weights of mice by sitagliptin and GLP-1(32-36)amide;

FIG. 7 is a graph showing changes in muscle weights of mice by sitagliptin and GLP-1(32-36)amide;

FIG. 8 is a graph showing changes in grip strengths of mice by sitagliptin and GLP-1(32-36)amide;

FIG. 9 is a graph showing changes in myostatin and MyoD expression by sitagliptin and GLP-1(32-36)amide;

FIG. 10 is a schematic experimental diagram for confirming the effects of improving muscle strength and muscle mass by GLP-1(7-36);

FIG. 11 is a graph showing results of grip strength measurement and four limbs hanging test of mice by GLP-1(7-36); A and B of FIG. 11 show changes in grip strength, and C and D show the results of four limbs hanging test;

FIG. 12 is a graph confirming the increase in muscle mass of mice by GLP-1(7-36). A of FIG. 12 shows total muscle mass of mice, and B to F of FIG. 12 show the measurement results of muscle mass of mice.

FIG. 13 is a graph comparing the sequences of dulaglutide and GLP-1.

DETAILED DESCRIPTION OF THE PREFERRED EMBODIMENTS

The present inventors have conducted various studies to develop hormone agents which may effectively treat sarcopenia or muscle atrophy or effectively slow progression thereof, and have focused on known hormone agents. These hormone agents are pharmaceutical compositions which were approved as having minimal side effects through predetermined levels of preclinical and clinical trials, and thus it was expected that selection of agents capable of treating or slowing sarcopenia or muscle atrophy from the hormone agents may solve the problems due to side effects. Accordingly, agents capable of treating or slowing sarcopenia or muscle atrophy were screened from the known hormone agents, and as a result, in addition to GLP-1, a GLP-1 fragment a GLP-1 derivative, and exendin-4, which are represented as glucagon-like peptide-1 receptor agonists, showing similar activity to GLP-1, were investigated.

Glucagon-like peptide-1 (GLP-1) is an incretin derived from a transcription product of a proglucagon gene, which is a prohormone, and is a hormone secreted by intestinal L cells by stimulation of intestinal nutrients or blood glucose level. Its major function is known to be stimulation of insulin secretion. For this reason, it has been studied and developed as a drug capable of effectively reducing blood glucose in the treatment of diabetes.

GLP-1 is mainly secreted in two forms of GLP-1(7-37) and GLP-1(7-36)amide, and they play a role in promoting insulin secretion by glucose by binding to a GLP-1 receptor. The secreted GLP-1(7-36)amide is also known to be metabolized in the form of GLP-1(9-36)amide.

The GLP-1(7-36) consists of 30 amino acids, and the amino acid sequence of GLP-1 is known to have a high identity between species in the active site. Specifically, the GLP-1(7-36) may include the amino acid sequence of SEQ ID NO: 4, but is not limited thereto.

Meanwhile, GLP-1 is degraded by an enzyme called 'DPP-4' and as a result, it loses its function. When a GLP-1 receptor agonist having resistance to the DPP-4 enzyme and serving an action similar to that of GLP-1 is administered to a patient, the functional effect of GLP-1 can be further enhanced.

Exendin-4, a kind of glucagon-like peptide-1 receptor agonist, is a peptide hormone agent that has a similar role to GLP-1, a glucagon analogue, and was developed to treat diabetes. Exendin-4 was administered to an animal in which sarcopenia and muscle atrophy were artificially induced, and its effects on sarcopenia or muscle atrophy were analyzed. As a result, it was found that muscular properties caused by sarcopenia or muscle atrophy, such as reduced body weight, skeletal muscle mass, grip strength, etc., were restored, expression of muscle protein-destroying genes was decreased, and expression of muscle protein-producing genes was increased. Further, other agonists of GLP-1R, which is a glucagon-like peptide-1 receptor, an analogue thereof, or an inhibitor inhibiting degradation of glucagon-like peptide-1, were expected to show equivalent levels of the effects.

As such, it was demonstrated that in addition to GLP-1, the GLP-1 fragment showing similar activity to GLP-1, the GLP-1 derivative, and exendin-4, which are represented as glucagon-like peptide-1 receptor agonists, have a novel effect of treating or slowing sarcopenia or muscle atrophy, in addition to the therapeutic effect on diabetes, and this novel effect has never been disclosed until now, and was demonstrated by the present inventors for the first time.

To achieve the above objects, an aspect of the present invention provides a pharmaceutical composition for preventing or treating muscle atrophy or sarcopenia including any one selected from the group consisting of glucagon-like peptide-1 (GLP-1), a GLP-1 fragment, a GLP-1 secretion enhancer, a GLP-1 receptor (GLP-1R, glucagon-like peptide-1 receptor) agonist, a GLP-1 secretion enhancer, a GLP-1 degradation inhibitor, and exendin-4.

As used herein, the term "GLP-1 (Glucagon-like peptide-1)" is an incretin derived from a glucagon precursor, and the glucagon precursor forms two types of glucagon, namely, GLP-1 and GLP-2, through a protein degradation process in vivo. The wild-type GLP-1, which is the initial product, has 37 amino acid residues (SEQ ID NO: 3), but as 6 amino acids are additionally removed from the amino terminus, the active form of GLP-1 (7-37) is formed. In addition, glycine, which is a residue at position 37 of GLP-1 (7-37), is modified to an amide to form GLP-1 (7-36) amide. Both GLP-1 (7-37) and GLP-1 (7-36) amide formed from GLP-1 act on the GLP-1 receptor and are known to have insulin-secreting ability. That is, not only the wild-type GLP-1, but also GLP-1 (7-37) and GLP-1 (7-36) amide produced therefrom bind to the GLP-1 receptor for their action and have the same activity as GLP-1.

Accordingly, in the present invention, the term "GLP-1" may refer not only to GLP-1, which is the initial product, but to GLP-1(7-37), GLP-1(7-36), GLP-1(9-36) etc., having the biological activity of GLP-1, which have been modified such that GLP-1 can have an in vivo activity.

In one embodiment of the present invention, it was confirmed that a long-acting peptide of GLP-1 (7-36) peptide (SEQ ID NO: 4), which is an active form of GLP-1, increased muscle strength and muscle mass in mice in which muscle atrophy was induced by dexamethasone (FIGS. 11 and 12), suggesting that GLP-1 has a therapeutic effect on muscle atrophy and sarcopenia.

As used herein, the term "GLP-1 fragment" refers to an amino acid sequence which is derived from the amino acid sequence of GLP-1 and prepared by any one method of substitution, addition, deletion, and modification of some amino acids in GLP-1, or a combination thereof. The GLP-1 fragment may be prepared by a method known to those skilled in the art. With respect to the objects of the present invention, any one may be included in the "GLP-1 fragment" of the present invention, as long as it is derived from GLP-1 and has the effects on muscle atrophy or sarcopenia. The GLP-1 fragment may include 5 or more, 10 or more, 15 or more, or 20 or more amino acids of the GLP-1 sequence. Specifically, the GLP-1 fragment may be GLP-1(28-36) amide or GLP-1(32-36)amide, and more specifically, the GLP-1 fragment may be GLP-1(32-36)amide (LVKGR amide) prepared by 5 amino acids of GLP-1, but is not limited thereto.

According to a specific embodiment of the present invention, the GLP-1(32-36)amide may have a sequence of SEQ ID NO: 2.

The present inventors confirmed that GLP-1(32-36) amide, a GLP-1 fragment, has a therapeutic effect on muscle atrophy or sarcopenia by increasing the body weight, muscle mass, and grip strength, decreasing expression of myostatin and increasing expression of MyoD in dexamethasone-treated mice, suggesting that therapeutic effects on muscle atrophy or sarcopenia may be obtained by the GLP-1 fragment (FIGS. 6 to 9).

As used herein, the term "GLP-1 receptor (GLP-1R, glucagon-like peptide-1 receptor)" refers to a receptor protein capable of binding with GLP-1 (glucagon-like peptide-1), which is a kind of gastrointestinal hormone derived from a transcript of a glucagon gene, and plays a role in reducing blood glucose levels. Specifically, the receptor binds with GLP-1 to increase transcription and expression of insulin gene via up-regulation of pancreatic duodenal homeobox-1 (PDX-1) which is a transcription factor.

As used herein, the term "GLP-1 receptor agonist (GLP-1R agonist)" refers to a substance or drug that binds to the GLP-1 receptor to act similarly to GLP-1, or a molecule that increases activity of a receptor site, and is also called an effector. The agonist is currently used as a therapeutic agent for type 2 diabetes, as its effect of increasing insulin secretion by binding to GLP-1 receptor was revealed.

Examples of the receptor agonist include GLP-1 and glucagon, which are known as natural agonists. In addition, there are liraglutide, exendin-4, lixisenatide, dulaglutide, albiglutide, etc.

With respect to the objects of the present invention, the GLP-1 receptor agonist includes any substance as long as it can bind to the GLP-1 receptor, like GLP-1, and have similar activity to GLP-1 via a similar signaling pathway, without limitation, and also includes any peptides or fragments thereof, precursor materials, variants, and derivatives capable of activating the GLP-1 receptor, and it may be a substance having a therapeutic effect on muscle atrophy or sarcopenia by increasing muscle mass and muscle strength, but is not limited thereto.

As used herein, the term "exendin-4" refers to a peptide that functions as a GLP-1 receptor agonist, and has a sequence consisting of 39 amino acids, a homology of about 53% with GLP-1 and a molecular weight of about 4 kDa. Since exendin-4 shows effects of rapidly regulating blood glucose levels, decreasing insulin resistance and glucagon levels, and promoting growth of pancreatic beta cells stimulating insulin production, it is used as a major therapeutic agent for diabetes with insulin resistance. An amino acid sequence of exendin-4 has an amino acid sequence of SEQ ID NO: 1, but is not particularly limited thereto.

In the present invention, exendin-4 is used an active ingredient of the pharmaceutical composition for treating muscle atrophy or sarcopenia, and exendin-4 may exhibit effects of increasing the body weight and skeletal muscle mass, inhibiting expression of muscle protein-destroying genes, and increasing expression of muscle protein-producing genes with respect to animals having muscle atrophy and sarcopenia. In this regard, examples of the muscle protein-destroying genes may include, but are not particularly limited to, genes encoding proteins such as myostatin, atrogin-1, MuRF1 (Muscle RING-finger protein-1), etc., and examples of the muscle protein-producing genes may include, but are not particularly limited to, genes encoding proteins such as MyoD, myogenin, etc.

The above-described therapeutic effects of exendin-4 on muscle atrophy or sarcopenia were unknown until now, and were demonstrated by the present inventors for the first time.

The present inventors confirmed that exendin-4 shows the effects of increasing the body weight and skeletal muscle mass, inhibiting expression of muscle protein-destroying genes, and increasing expression of muscle protein-producing genes, and thus exendin-4 may be used in the prevention and treatment of muscle atrophy or sarcopenia.

Figure 13:
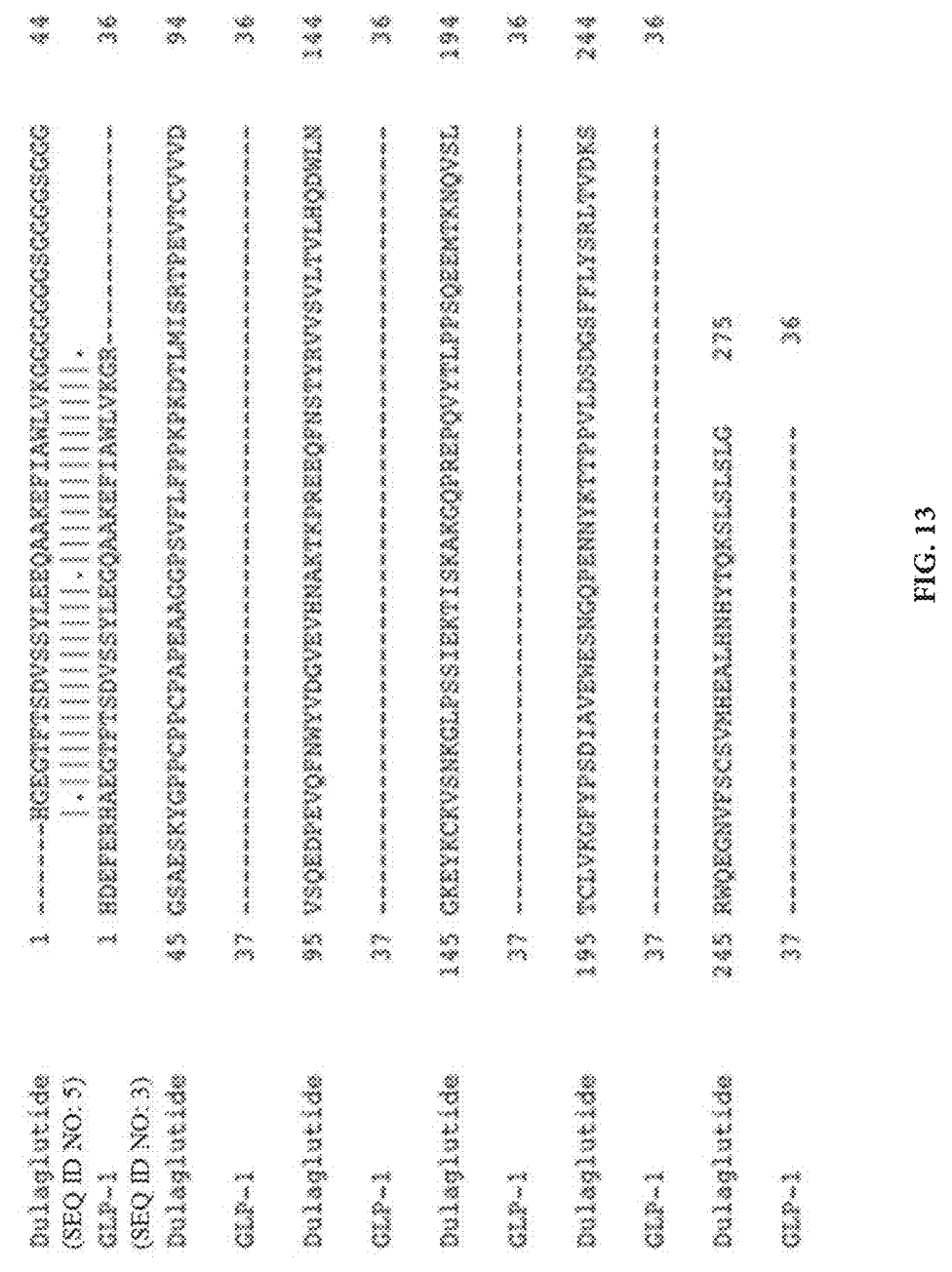

As used herein, the term "dulaglutide" is one of the GLP-1 receptor agonists, is a drug in which GLP-1 and a human-derived IgG4 are covalently bound, and is also known by the trade name Trulicity. In order to complement the half-life of GLP-1, which has a short half-life, it is in the form in which IgG4 is bound to the GLP-1 moiety as a carrier, and is a long-acting drug being used as a therapeutic agent for the treatment of type 2 diabetes, which is currently administered once a week. The GLP-1 moiety corresponds to GLP-1 (7-36) and includes substitution of some amino acid residues (ABG, G22E, R36G) compared to native GLP-1 and has a homology of 97% with the native GLP-1 (FIG. 13). The sequence of dulaglutide may be represented by amino acids of SEQ ID NO: 5.

Meanwhile, the exendin-4 or dulaglutide are both examples of the GLP-1 receptor agonist and have similar activity to GLP-1 by binding to the GLP-1 receptor. That is, in the present invention, it was confirmed that GLP-1, and exendin-4 and dulaglutide, which are GLP-1 receptor agonists, are drugs that act on the GLP-1 receptor and show an effect on muscle atrophy or sarcopenia. Thus, other substances which can show an activity by binding to the GLP-1 receptor (that is, the GLP-1 receptor agonists), in addition to GLP-1, can also show similar preventive or therapeutic effect on muscle atrophy or sarcopenia.

As used herein, the term "GLP-1 secretion enhancer" refers to an agent capable of increasing GLP-1 secretion. Specific examples of the "GLP-1 secretion enhancer" may include G-protein coupled receptor 119 agonist, but are not limited thereto.

In the present invention, the GLP-1 secretion enhancer exhibits equivalent effects to GLP-1 or GLP-1 receptor agonist (the effects of increasing the skeletal muscle mass, inhibiting expression of muscle protein-destroying genes, and increasing expression of muscle protein-producing genes) by increasing GLP-1 secretion, and therefore, it may be used as an active ingredient of the pharmaceutical composition for preventing or treating sarcopenia or muscle atrophy.

As used herein, the term "GLP-1 degradation inhibitor" refers to an agent capable of maintaining the actions of GLP-1 by inhibiting GLP-1 degradation. The GLP-1 degradation inhibitor is a DPP-4 inhibitor, etc., but is not particularly limited thereto.

According to a specific embodiment of the present invention, the GLP-1 degradation inhibitor may be a DPP-4 (dipeptidyl peptidase-4) inhibitor.

As used herein, the term "DPP-4 (dipeptidyl peptidase-4) inhibitor" refers to an enzyme inhibiting DPP-4 enzyme which is known to degrade GLP-1, and maintains high concentrations of GLP-1 by inhibiting DPP-4. Specifically, the inhibitor may be vildagliptin, sitagliptin, or saxagliptin, and more specifically, sitagliptin, but is not limited thereto.

In the present invention, the GLP-1 degradation inhibitor acts to maintain GLP-1 concentration by inhibiting degradation of GLP-1, and consequently, it may have the therapeutic effect on muscle atrophy or sarcopenia, similar to GLP-1 or the GLP-1 receptor agonist.

The present inventors confirmed that sitagliptin shows effects of increasing the body weight, skeletal muscle mass, and grip strength, inhibiting myostatin expression, and increasing MyoD expression in dexamethasone-treated mice, and therefore, sitagliptin exhibits therapeutic effects on muscle atrophy or sarcopenia (FIGS. 6 to 9).

The GLP-1 or a fragment thereof, the GLP-1 receptor agonist, the GLP-1 secretion enhancer, the GLP-1 degradation inhibitor, or the exendin-4 of the present invention may include amino acid sequences having a homology of more than 70%, specifically more than 80%, more specifically more than 90%, even more specifically more than 91%, 92%, 93%, 94%, 95%, 96%, 97%, 98%, or 99%, to the GLP-1 or a fragment thereof, the GLP-1 receptor agonist, the GLP-1 secretion enhancer, the GLP-1 degradation inhibitor, or the exendin-4 as long as they function in the same manner to show a therapeutic effect on muscle atrophy or sarcopenia, but is not limited thereto.

As used herein, the term 'homology' is intended to indicate the degree of similarity to the amino acid sequence of a wild type protein or a base sequence encoding the same and includes sequences having a homology of the above percentage or higher with the amino acid sequence or base sequence of the present invention. The homology may be determined by comparing the two given sequences by the naked eye, but may be determined using a bioinformatic algorithm, which enables the analysis of a homology by arranging the subject sequences for comparison. The homology between the two given amino acid sequences may be indicated as a percentage. The useful automated algorithm is available for use in GAP, BESTFIT, FASTA, and TFASTA computer software modules of the Wisconsin Genetics Software Package (Genetics Computer Group, Madison, Wis., USA). The arrangement algorithm automated in the above modules includes sequence arrangement algorithm by Needleman & Wunsch, Pearson & Lipman, and Smith & Waterman. Other useful algorithms on sequence arrangement and homology determination are automated in software including FASTP, BLAST, BLAST2, PSIBLAST, and CLUSTAL W.

The information of the sequences of the GLP-1 or a fragment thereof, the GLP-1 receptor agonist, the GLP-1 secretion enhancer, the GLP-1 degradation inhibitor, or the exendin-4 and the base sequences encoding the same may be obtained from database known in the art, such as NCBI, etc.

Although GLP-1, exendin-4, etc. of the present invention are represented as specific sequence numbers, the peptide is not limited to a specific sequence, and they may fall within the scope of the present invention, as long as they have substantially the same activity, while having a homology of predetermined level or higher with the above peptide. In addition, peptides well known in the art including substitution, addition, deletion, modification etc. of amino acid residues which can be performed to increase the stability and half-life of the peptide without affecting the peptide activity may also fall within the scope of the present invention.

In the present invention, examples of GLP-1 or a fragment thereof, the GLP-1 receptor agonist, the GLP-1 secretion enhancer, the GLP-1 degradation inhibitor, or the exendin-4 may include variants, derivatives, fragments, long-acting formulations, etc., of the GLP-1 or a fragment thereof, the GLP-1 receptor agonist, the GLP-1 secretion enhancer, the GLP-1 degradation inhibitor, or the exendin-4.

As used herein, the term "variant" refers to a peptide having one or more amino acid sequences different from those of GLP-1 or a fragment thereof, the GLP-1 receptor agonist, the GLP-1 secretion enhancer, the GLP-1 degradation inhibitor, or the exendin-4, and may refer to a substance that can bind particularly to the GLP-1 receptor and can have a therapeutic effect on muscle atrophy and sarcopenia. Specifically, the variant may be prepared by any one of substitution, addition, deletion, and modification or by a combination thereof in a part of the native amino acid sequences.

As used herein, the term "derivative" may include peptides, peptide derivatives, or peptide mimetics capable of activating the GLP-1 receptor by modifying a part of amino acid of GLP-1 or a fragment thereof, the GLP-1 receptor agonist, the GLP-1 secretion enhancer, the GLP-1 degradation inhibitor, or the exendin-4 via addition, deletion, or substitution.

As used herein, the term "fragment" refers to a fragment having one or more amino acids added or deleted at the N-terminus or the C-terminus of GLP-1 or a fragment thereof, the GLP-1 receptor agonist, the GLP-1 secretion enhancer, the GLP-1 degradation inhibitor, or the exendin-4. The added amino acids may possibly be non-naturally occurring amino acids (e.g., D-type amino acids).

As used herein, the term "long-acting" refers to a form of a drug prepared so as to increase the half-life of GLP-1 or a fragment thereof, the GLP-1 receptor agonist, the GLP-1 secretion enhancer, the GLP-1 degradation inhibitor, or the exendin-4, which are active ingredients of the present invention.

In the present invention, the GLP-1 or a fragment thereof, the GLP-1 receptor agonist, the GLP-1 secretion enhancer, the GLP-1 degradation inhibitor, or the exendin-4 may be administered alone to a subject to have a therapeutic effect on muscle atrophy or sarcopenia or may be a long-acting type, wherein a biocompatible material or a carrier is linked by a linker or a covalent bond. Specifically, a biocompatible material or a carrier may be directly linked to the GLP-1 or a fragment thereof, the GLP-1 receptor agonist, the GLP-1 secretion enhancer, the GLP-1 degradation inhibitor, and the exendin-4 via a covalent bond by a known genetic recombination technique, etc.

Although such a long-acting type drug has an identical sequence to that of the active ingredients, it may have an enhanced half-life or bioavailability compared to non-long-acting type.

As used herein, the terms "biocompatible material" and "carrier" refer to materials which can directly or indirectly increase the duration of the activity of GLP-1 or a fragment thereof, the GLP-1 receptor agonist, the GLP-1 secretion enhancer, the GLP-1 degradation inhibitor, or the exendin-4 when the biocompatible material and the carrier are covalently or non-covalently linked to the GLP-1 or a fragment thereof, GLP-1 receptor agonist, GLP-1 secretion enhancer, GLP-1 degradation inhibitor, or exendin-4 of the present invention.

Examples of the biocompatible material or carrier may include, but are not limited to, high molecular weight polymers such as polyethylene glycol, polypropylene glycol, ethylene glycol-propylene glycol copolymers, polyoxyethylated polyol, polyvinyl alcohol, dextran, polyvinyl ethyl ether, biodegradable polymers, lipid polymers, chitin, or hyaluronic acid, and fatty acids, cholesterol, albumin and fragments thereof, albumin-binding substances, antibodies, antibody fragments, immunoglobulin Fc regions, nucleotides, fibronectin, transferrin, saccharides, etc. In addition, the above-described carriers or biocompatible materials may be used in a combination of two or more thereof.

In addition, the immunoglobulin Fc region is not only advantageous in terms of the preparation, purification, and yield of the drug, because the molecular weight is relatively small compared to the entire molecule, but also it can be expected that the homogeneity of the materials is also greatly increased and the potential of inducing antigenicity in blood is lowered, as the amino acid sequences are different in each antibody, and thus the Fab portion showing a high non-homogeneity is removed. The immunoglobulin Fc region may be a native type, but it may be a derivative modified to be more suitable as the carrier of a drug, and methods of preparing various Fc region derivatives are known in the art.

The method by which the biocompatible material or the carrier is linked to the GLP-1 or a fragment thereof, the GLP-1 receptor agonist, the GLP-1 secretion enhancer, the GLP-1 degradation inhibitor, or the exendin-4 includes a genetic recombination method and an in vitro linkage using polymers or low molecular chemicals, but is not limited to any of the linking methods.

The linker that links the carrier capable of increasing the in vivo half-life of the peptide may consist of peptides, polyethylene glycols, fatty acids, saccharides, high molecular weight polymers, low molecular weight compounds, nucleotides, and a combination thereof, and may be any chemical bond such as a non-covalent chemical bond, a covalent chemical bond, etc., but is not limited thereto.

In addition, the long-acting type drug may be prepared by substitution, addition, deletion, and modification of some amino acids on the GLP-1 or a fragment thereof, the GLP-1 receptor agonist, the GLP-1 secretion enhancer, the GLP-1 degradation inhibitor, or the exendin-4.

For example, those prepared to have resistance to a degradation enzyme of a peptide through modification of some amino acid residues, those in which some amino acid residues that affect the binding strength with respect to a peptide receptor are modified, or those in which some amino acid residues are modified to increase the stability of the peptide may be included in the scope of the present invention.

Methods of preparing the above-described long-acting type drugs are well known in the art and may be appropriately selected and performed by those skilled in the art.

As used herein, the term "muscle atrophy" collectively refers to a disease in which muscles of the legs and arms are gradually atrophied almost symmetrically, and muscle atrophy may accompany the occurrence of cancer, aging, renal diseases, genetic diseases, and various chronic diseases. Muscle atrophy is represented by amyotrophic lateral sclerosis (Lou Gehrig's disease), spinal progressive muscular atrophy, Duchenne muscular dystrophy, etc.

As used herein, the term "sarcopenia" refers to gradual weakness of density and functions of muscles, and is known to be caused by progressive modification and degradation of motor neurons or myocytes in the spinal cord or diencephalon. In particular, muscle loss due to aging is called age-related sarcopenia.

Since muscle atrophy and sarcopenia are diseases that accompany reduction and attenuation of muscles, an increase in muscle strength and muscle mass may be a possible treatment method for muscle atrophy and sarcopenia. The present inventors confirmed that GLP-1 (7-36), exendin-4, GLP-1(32-36) amide, and sitagliptin show the effects of increasing body weight, muscle mass, and grip strength, decreasing myostatin expression, and increasing MyoD expression in mouse models in which sarcopenia and muscle atrophy were induced by dexamethasone, thereby confirming therapeutic effects on muscle atrophy and sarcopenia.

In the present invention, the muscle atrophy or sarcopenia may be treated by using glucagon-like peptide-1, the GLP-1 fragment, the GLP-1 secretion enhancer, the GLP-1 degradation inhibitor, the GLP-1 receptor agonist, or exendin-4, and therapeutic effects thereof may be equivalently applied to muscle atrophy as well as sarcopenia caused variously by, for example, cancer, aging, renal diseases, etc.

According to an Example of the present invention, dexamethasone-induced sarcopenia or muscle atrophy mice and sarcopenia or muscle atrophy-induced mice were treated with dulaglutide, and the effect of dulaglutide on the muscle strength and muscle mass of the mouse models was examined. As a result, the grip strength and muscle strength of the mice were enhanced (FIG. 11), and the muscle mass was increased (FIG. 12).

According to another Example of the present invention, dexamethasone-induced sarcopenia or muscle atrophy mice and sarcopenia or muscle atrophy mice as animal models were treated with a vehicle (PBS) or exendin-4, respectively, and these mice were used to examine the effect of exendin-4 on the mouse models. As a result, when the mice were treated with exendin-4, reduced body weight was restored (FIG. 1), and reduced skeletal muscle mass was restored (FIG. 2), reduced grip strength was restored (FIG. 3), and increased expression levels of muscle protein-destroying genes (myostatin, atrogin-1, and MuRF1) by dexamethasone were decreased, whereas expression levels of muscle protein-producing genes (MyoD and myogenin) were increased (FIG. 4).

Therefore, it can be seen that GLP-1 or the glucagon-like peptide-1 receptor agonist may be used as an active ingredient of the pharmaceutical composition for treating muscle atrophy or sarcopenia.

The composition of the present invention may be prepared in the form of a pharmaceutical composition for preventing or treating muscle atrophy or sarcopenia further including appropriate carriers, excipients, or diluents which are commonly used in the preparation of pharmaceutical compositions. Specifically, the pharmaceutical composition may be formulated according to common methods into oral dosage forms such as powders, granules, tablets, capsules, suspensions, emulsions, syrups, aerosols, etc., external dosage forms, suppositories, or sterile injectable solutions. In the present invention, the carriers, excipients, and diluents included in the pharmaceutical composition may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, and minerals. These formulations may be prepared by using a commonly used diluent or excipient, such as a filler, an extender, a binder, a wetting agent, a disintegrant, a surfactant, etc. Examples of a solid formulation for oral administration include a tablet, a pill, a powder, a granule a capsule, etc. These solid formulations are prepared by mixing the extract or a fraction thereof with at least one excipient, for example, starch, calcium carbonate, sucrose, lactose, gelatin, etc. A lubricant such as magnesium stearate or talc may also be used in addition to the simple excipient. Examples of a liquid formulation for oral administration include a suspension, a solution for internal use, an emulsion, a syrup, etc. The liquid formulation may include, in addition to liquid paraffin or water, a commonly available simple diluent, various excipients, such as a wetting agent, a sweetener, an aromatic, a preservative, etc. A formulation for parenteral administration may include a sterilized aqueous solution, a non-aqueous solvent, a suspension, an emulsion, a lyophilized formulation, and a suppository. The non-aqueous solvent and the suspension may be propylene glycol, polyethylene glycol, a plant oil such as olive oil, or an injectable ester such as ethyloleate. A base for the suppository formulation may be witepsol, macrogol, tween 61, cacao butter, laurin butter, glycerogelatin, etc.

A content of the glucagon-like peptide-1 receptor agonist in the pharmaceutical composition of the present invention may be, but is not particularly limited to, for example, 0.0001% by weight to 10% by weight, and for another example, 0.01% by weight to 3% by weight.

The pharmaceutical composition of the present invention may be administered in a pharmaceutically effective amount. As used herein, the term "pharmaceutically effective amount" refers to an amount sufficient to treat or prevent diseases at a reasonable benefit/risk ratio applicable to any medical treatment or prevention, and the effective dosage level may be determined depending on factors including severity of the disease, activity of the drug, a patient's age, body weight, health, and sex, sensitivity to the drug, administration time, administration route, and excretion rate of the composition of the present invention, duration of treatment, drugs used simultaneously or in combination with the composition of the present invention, and other factors known in the medical field. The pharmaceutical composition of the present invention may be administered alone or in combination with other known therapeutic agents for muscle atrophy or sarcopenia. It is important to administer the composition in a minimum amount that may exhibit a maximum effect without causing side effects, in view of all of the above-described factors.

An administration dose of the pharmaceutical composition of the present invention may be determined by a skilled person in the art considering the intended use(s), severity of disease(s), age, body weight, sex, and anamnesis of a patient, or kinds of ingredients used as active ingredient(s), etc. For example, the pharmaceutical composition of the present invention may be administered in an amount of about 0.1 ng/kg to about 100 mg/kg per adult, preferably about 1 ng/kg to about 10 mg/kg per adult, and administration frequency of the composition of the present invention is not particularly limited, but the composition of the present invention may be administered once daily or in divided doses. The administration dose does not limit the scope of the present invention in any aspect.

Another aspect of the present invention provides a method of treating sarcopenia or muscle atrophy, including administering a pharmaceutically effective amount of the pharmaceutical composition to a subject with sarcopenia or muscle atrophy.

The method for treating sarcopenia or muscle atrophy may be achieved by administering a composition including GLP-1 or a fragment thereof, a GLP-1 receptor agonist, a GLP-1 secretion enhancer, a GLP-1 degradation inhibitor, or exendin-4 to a subject, and thus enhancing muscle strength and muscle mass of the subject with sarcopenia or muscle atrophy by the action of GLP-1 or a fragment thereof, the GLP-1 receptor agonist, the GLP-1 secretion enhancer, the GLP-1 degradation inhibitor, or the exendin-4 of the composition.

As used herein, the term "subject" includes all mammalian animals including mice, livestock, and humans, or cultured fish which may have sarcopenia or muscle atrophy or have already had sarcopenia or muscle atrophy, without limitation.

The pharmaceutical composition for treating muscle atrophy or sarcopenia of the present invention may be administered via any of the common routes, as long as it is able to reach a desired tissue. The pharmaceutical composition of the present invention may be administered intraperitoneally, intravenously, intramuscularly, subcutaneously, intradermally, orally, intranasally, intrapulmonarily, or intrarectally according to the desired purpose, but the present invention is not particularly limited thereto. However, since the GLP-1 or a fragment thereof, the GLP-1 receptor agonist, the GLP-1 secretion enhancer, the GLP-1 degradation inhibitor, or the exendin-4 may be denatured by gastric acid upon oral administration, active ingredients of a composition for oral administration should be coated or formulated for protection against degradation in the stomach. In addition, the composition may be administered using a certain apparatus capable of transporting the active ingredients into a target cell.

Still another aspect of the present invention provides use of the pharmaceutical composition in the preparation of a drug for preventing or treating muscle atrophy or sarcopenia.

Mode for Invention

Hereinafter, the present invention will be described in more detail with reference to Examples. However, these Examples are for illustrative purposes only, and the scope of the present invention is not intended to be limited by these Examples.

Example 1

Investigation of Therapeutic Effect of Exendin-4 on Muscle Atrophy or Sarcopenia Example 1-1

Effect of Exendin-4 on Body Weight of Muscle Atrophy-Induced Animal

It is known that muscle atrophy is caused by chronic diseases (chronic renal failure, chronic heart failure, chronic obstructive disease, etc.), and caused by administration of a high dose of a drug such as dexamethasone. Thus, animal models (C57BL/6J male mice) were treated with dexamethasone to prepare sarcopenia models. When sarcopenia occurred, effects of exendin-4 were investigated.

In detail, control mice which were not administered with dexamethasone or exendin-4, mice in which muscle atrophy was induced by intraperitoneal injection of dexamethasone (200 mg/kg) for 8 days, comparative mice which were intraperitoneally injected with exendin-4 (100 ng/mouse) for 12 days, and mice in which muscle atrophy was treated by intraperitoneal injection of exendin-4 (100 ng/mouse) for 12 days following intraperitoneal injection of dexamethasone (200 mg/kg) for 8 days were prepared. While these mice were raised for 20 days, changes in their body weights were measured (FIG. 1).

FIG. 1 is a graph showing changes in the body weights which were measured in control mice, comparative mice, muscle atrophy-induced mice, and muscle atrophy-treated mice while they were raised for 20 days. As shown in FIG. 1, increase in the body weight was observed in the mice treated with combination of dexamethasone and exendin-4, compared to the mice treated with dexamethasone alone, from the elapsed time of 11 days.

Therefore, it can be seen that exendin-4 exhibits the effect of improving symptoms of muscle atrophy-induced mice.

Example 1-2

Effect of Exendin-4 on Muscle Mass of Muscle Atrophy-Induced Animal

The control mice (control), dexamethasone-induced muscle atrophy mice, exendin-4-treated comparative mice, and muscle atrophy-treated mice treated with exendin-4 following treatment of dexamethasone, which were prepared in Example 1-1, were sacrificed, and total weights of the skeletal muscles of the respective mice were measured. Quadratus muscles, gastrocnemius muscles, tibialis anterior muscles, soleus muscles, and extensor digitorum longus muscles constituting the skeletal muscles were each separated, and their weights were compared (FIG. 2).

FIG. 2 is a graph showing results of comparing weights of respective skeletal muscles which were obtained from control mice, comparative mice, muscle atrophy-induced mice, and muscle atrophy-treated mice. As shown in FIG. 2, muscle atrophy-induced mice showed a reduction in the muscle mass of all kinds of skeletal muscles, as compared with the control and comparative group, whereas muscle atrophy-treated mice showed increased muscle mass similar to that of the control or comparative group.

Example 1-3

Effect of Exendin-4 on Grip Strength of Muscle Atrophy-Induced Animal

The control mice (control), dexamethasone-induced muscle atrophy mice, exendin-4-treated comparative mice, and muscle atrophy-treated mice treated with exendin-4 following treatment of dexamethasone, which were prepared in Example 1-1, were subjected to measurement of grip strength to investigate whether muscle functions were recovered (FIG. 3). In this regard, a force measured by a grip strength machine when all of the paws of a mouse were pulled with the same force was considered as the grip strength.

FIG. 3 is a graph showing results of comparing grip strengths which were measured in control mice, comparative mice, muscle atrophy-induced mice, and muscle atrophy-treated mice. As shown in FIG. 3, it was found that the muscle atrophy-induced mice showed the lowest level of grip strength whereas muscle atrophy-treated mice showed a slightly lower level of grip strength than the control and comparative mice, but a remarkably higher level of grip strength than the muscle atrophy-induced mice.

Example 1-4

Effect of Exendin-4 on Expression Levels of Muscle Protein-Producing Genes and Muscle Protein-Destroying Genes in Muscle Atrophy-Induced Animal It is known that when muscle atrophy occurs, expression of muscle protein-destroying genes (myostatin, atrogin-1, and MuRF1) is increased and expression of muscle protein-producing genes (MyoD and myogenin) is decreased; thus, this was to be examined That is, muscle tissues were removed from the control mice (control), dexamethasone-induced muscle atrophy mice, exendin-4-treated comparative mice, and muscle atrophy-treated mice treated with exendin-4 following treatment of dexamethasone, which were prepared in Example 1-1, and total RNAs were obtained from the muscle tissues. cDNAs were synthesized therefrom, each gene was amplified from the synthesized cDNA by PCR, and changes in the expression levels thereof were compared (FIG. 4).

FIG. 4 is a graph showing results of comparing expression levels of muscle protein-destroying genes (myostatin, atrogin-1, and MuRF1) and muscle protein-producing genes (MyoD and myogenin) in the muscles of control mice, comparative mice, muscle atrophy-induced mice, and muscle atrophy-treated mice. As shown in FIG. 4, the highest relative expression levels of muscle protein-destroying genes (myostatin, atrogin-1, and MuRF1) and lowest relative expression levels of muscle protein-producing genes (MyoD and myogenin) were observed in the muscle tissues of the muscle atrophy-induced mice. In contrast, the lowest relative expression levels of muscle protein-destroying genes (myostatin, atrogin-1, and MuRF1) and highest relative expression levels of muscle protein-producing genes (MyoD and myogenin) were observed in the muscle tissues of the muscle atrophy-treated mice.

Example 1-5

Effect of Exendin-4 on Expression Levels of Muscle Atrophy-Related Genes at Cell Level A myoblast cell line C2C12 was differentiated into myocytes by culturing in a medium containing 2% (v/v) horse serum for 5 days. Control myocytes (control) prepared from the differentiated myocytes without any treatment, myocytes in which muscle atrophy symptoms were induced by treatment of 1 µM dexamethasone for 12 hours, comparative myocytes treated with 20 nM exendin-4 for 6 hours, and experimental myocytes in which muscle atrophy symptoms were treated with 20 nM exendin-4 for 6 hours following treatment of 1 µM dexamethasone for 12 hours were each prepared. Expression levels of muscle atrophy-related genes (myostatin, atrogin-1, and MuRF1) were compared in each of the myocytes (FIG. 5).

FIG. 5 is a graph showing results of comparing expression levels of muscle atrophy-related genes (myostatin, atrogin-1, and MuRF1) in control myocytes, muscle atrophy symptom-induced myocytes, comparative myocytes, and muscle atrophy symptom-treated myocytes. As shown in FIG. 5, the highest relative expression levels of the genes (myostatin, atrogin-1, and MuRF1) were observed in the muscle atrophy symptom-induced myocytes. In contrast, the muscle atrophy symptom-treated myocytes showed remarkably decreased expression levels of the genes (myostatin, atrogin-1, and MuRF1), similar to the levels of the control myocytes.

Taken together, the results of Examples 1-1 to 1-5 show that exendin-4 exhibits the effects of treating, improving, or recovering dexamethasone-induced muscle atrophy or sarcopenia.

In addition, the present inventors intended to investigate therapeutic effects of GLP-1, which shows the similar activity as exendin-1, on muscle atrophy or sarcopenia.

In this regard, they intended to investigate the function GLP-1(7-36), an active form of GLP-1, on dexamethasone-induced muscle atrophy or sarcopenia mice. Specifically, the effects of GLP-1(7-36) were confirmed using Trulicity, which is a long-acting formulation of GLP-1(7-36), as follows:

Example 2

Investigation of Therapeutic Effect of GLP-1 (7-36) on Muscle Atrophy or Sarcopenia

Example 2-1

Experimental Method

The experimental method of the Example was schematically illustrated in FIG. 10.

Specifically, 10-week-old male C57BL6J mice were divided into 10 mice per group (total n=40), and saline and dexamethasone (20 mg/kg) were each intraperitoneally administered to the control and experimental groups each day. The grip strength of the mice was measured on day 9.

Subsequently, on day 11, the control mice were administered with saline three times per week by subcutaneous injection (Co-vehicle group), whereas the comparative mice were administered with either (i) saline three times per week by subcutaneous injection (Dex-vehicle group), (ii) Trulicity (SEQ ID NO: 5) two times per week by subcutaneous injection (1 mg/kg; Trulicity group), or (iii) PB1023 three times per week by subcutaneous injection (3 mg/kg; PB1023 group).

Both Trulicity and PB1023 are long-acting formulations of GLP-1. Trulicity is a drug in which GLP-1 is covalently linked to human IgG4, and PB1023 is a recombinant analogue of GLP-1 and is being developed as a therapeutic agent for diabetes. PB1023 is a long-acting GLP-1 currently under development as a therapeutic agent for diabetes by Phasebio, a pharmaceutical company, and is a drug which has completed Phase 2 clinical trials.

Thereafter, the grip strength was measured and a four limb hanging test was performed on day 14, and tissue sampling was performed on day 22.

Example 2-2

Confirmation of Improvement of Grip Strength and Muscle Strength by GLP-1 (7-36)

The change in the grip strength after two weeks of the administration of the drug, which was measured by above method, was analyzed, and as a result, it was confirmed that the grip strength was improved to a significant level in the Trulicity or PB1023 drug administration groups (FIGS. 11A and 11B). Similar tendencies were observed in the results of the four limbs hanging test (C and D of FIG. 11).

Example 2-3

Confirmation of Increase in Muscle Mass by GLP-1 (7-36)

The total muscle mass after three weeks of the administration of the drug, which was measured by the above method, was analyzed, and as a result, it was confirmed that the total muscle mass of mice in the Trulicity or PB1023 drug administration group was significantly increased compared to the Dex-vehicle group, and the level of increase was similar to that of the Co-vehicle group (FIG. 12A).

In addition, the tendency of increasing muscle mass was also confirmed for each muscle type of TA (Tibialis anterior), Sol (Soleus), and GA (Gastrocnemius), and statistical significance was confirmed by an increase in muscle mass of EDL (Extensor digitorum longus) and QD (Quadratus) (B to F of FIG. 12).

It was confirmed from the Examples that GLP-1 (7-36) show the effects of increasing muscle strength and muscle mass in the muscle atrophy models, and therefore, it was confirmed once again that GLP-1 (7-36) has therapeutic effects on muscle atrophy or sarcopenia Furthermore, the present inventors intended to investigate therapeutic effects of GLP-1 degradation inhibitor and GLP-1 fragment on muscle atrophy or sarcopenia, in addition to exendin-4 and GLP-1. Thus, changes of the body weight, muscle, grip strength, and genes by sitagliptin, which is known as a GLP-1 degradation inhibitor, and GLP-1(32-36)amide were examined in animal models.

Example 3: Examination of Therapeutic Effect of Sitagliptin and GLP-1(32-36)Amide on Muscle Atrophy or Sarcopenia

Example 3-1

Effects of Sitagliptin and GLP-1(32-36)Amide on Body Weight and Muscle of Muscle Atrophy Animal Model The present inventors treated C57BL/6J male mice (n=10/group) with dexamethasone (20 mg/kg/i.p.) to reduce muscles of the mice, and they examined effects of sitagliptin (300 mg/kg/oral gavage) and GLP-1(32-36)amide (5 μg/kg/i.p.) on the body weights and muscles of the mice.

As a result, it was found that the body weight (FIG. 6) and muscle mass (FIG. 7) reduced by dexamethasone were increased by sitagliptin or GLP-1(32-36)amide.

Example 3-2

Effects of Sitagliptin and GLP-1(32-36)Amide on Grip Strength of Muscle Atrophy Animal Model The present inventors confirmed in Example 3-1 that the body weight and muscle mass were increased by sitagliptin, and accordingly, they also examined whether grip strengths of the mice were increased in order to examine whether muscle functions were actually increased by the increased body weight and muscle mass.

In detail, the grip strength when all of the paws of the mouse of Example 6 were pulled with the same force was measured by a grip strength machine.

As a result, it was found that grip strength reduced by dexamethasone was increased again by sitagliptin and GLP-1(32-36)amide (FIG. 8).

Example 3-3

Effects of Sitagliptin and GLP-1(32-36)Amide on Expression Level of Genes Related to Muscle Protein Production and Destruction of Muscle Atrophy Animal Model As described above, muscle atrophy is caused by increased expression of genes destroying proteins constituting muscles and inhibited expression of genes producing the proteins.

Therefore, the present inventors examined a change in the expression level of myostatin, which is a cause of muscle atrophy, and a change in the expression level of the muscle-producing factor MyoD by sitagliptin and GLP-1(32-36) amide.

As a result, myostatin expression was increased by dexamethasone, but decreased again by sitagliptin and GLP-1 (32-36)amide. In contrast, MyoD expression was decreased by dexamethasone, but increased again by sitagliptin and GLP-1(32-36)amide (FIG. 9).

From the results of Examples 3-1 to 3-2, the present inventors confirmed that sitagliptin, a GLP-1 degradation inhibitor, or GLP-1(32-36)amide, a GLP-1 fragment, as well as GLP-1 or exendin-4, a receptor agonist thereof, has the therapeutic effect on sarcopenia or muscle atrophy.

Based on the above description, it will be understood by those skilled in the art that the present invention may be implemented in a different specific form without changing the technical spirit or essential characteristics thereof. Therefore, it should be understood that the above embodiment is not limitative, but illustrative in all aspects. The scope of the invention is defined by the appended claims rather than by the description preceding them, and therefore all changes and modifications that fall within metes and bounds of the claims, or equivalents of such metes and bounds are therefore intended to be embraced by the claims.

What is claimed is:

1. A method for treating muscle atrophy or sarcopenia, comprising administering an effective amount of a pharmaceutical composition comprising glucagon-like peptide-1 (GLP-1) or a GLP-1 fragment to a subject having muscle atrophy or sarcopenia, wherein the GLP-1 or the GLP-1 fragment includes the amino acid sequence of SEQ ID NO: 4.

2. The method of claim 1, wherein the GLP-1 is a long-acting type to which an immunoglobulin Fc region is linked.

3. The method of claim 1, wherein the pharmaceutical composition exhibits an effect selected from the group consisting of effects of increasing body weight, increasing skeletal muscle mass, increasing expression of muscle protein-producing genes, inhibiting expression of muscle protein-destroying genes, enhancing muscle strength, and combinations thereof.

4. The method of claim 3, wherein the muscle protein-destroying gene is a gene encoding myostatin, atrogin-1, or MuRF1 (muscle RING-finger protein-1).

5. The method of claim 3, wherein the muscle protein-producing gene is a gene encoding MyoD or myogenin.

6. The method of claim 1, wherein the composition further comprises a pharmaceutically acceptable carrier, excipient, or diluent.

* * * * *